(12) United States Patent
Watts

(10) Patent No.: US 11,291,460 B2
(45) Date of Patent: Apr. 5, 2022

(54) HOLSTER AND TOURNIQUET DEVICE AND METHOD OF USE

(71) Applicant: Randy Watts, Spokane, WA (US)

(72) Inventor: Randy Watts, Spokane, WA (US)

( * ) Notice: Subject to any disclaimer, the term of this patent is extended or adjusted under 35 U.S.C. 154(b) by 0 days.

(21) Appl. No.: 16/927,439

(22) Filed: Jul. 13, 2020

(65) Prior Publication Data

US 2021/0022749 A1 Jan. 28, 2021

Related U.S. Application Data

(60) Provisional application No. 62/879,530, filed on Jul. 28, 2019.

(51) Int. Cl.
*A61B 17/132* (2006.01)
*F41C 33/04* (2006.01)
*A61B 17/00* (2006.01)

(52) U.S. Cl.
CPC ........ *A61B 17/1327* (2013.01); *F41C 33/046* (2013.01); *A61B 2017/00951* (2013.01)

(58) Field of Classification Search
CPC ............ A61B 17/1327; A61B 17/1322; A61B 17/132; A61B 17/1325; F41C 33/041; F41C 33/043; F41C 33/046; F41C 33/02; F41C 33/0209; F41C 33/0227
See application file for complete search history.

(56) References Cited

U.S. PATENT DOCUMENTS

| | | | |
|---|---|---|---|
| 5,058,788 A | 10/1991 | Newmark | |
| 7,954,204 B2 | 6/2011 | Hammerslag et al. | |
| 7,981,135 B2 | 7/2011 | Thorpe | |
| 8,424,168 B2 | 4/2013 | Soderberg et al. | |
| 9,333,128 B2 | 5/2016 | Catrone | |
| 10,492,568 B2 | 12/2019 | Burns et al. | |
| 2005/0198872 A1* | 9/2005 | Correa | F41C 33/041 36/136 |
| 2015/0257767 A1* | 9/2015 | Henderson | A61B 17/1327 606/203 |
| 2016/0128700 A1* | 5/2016 | Fry | A61B 17/1322 606/203 |
| 2016/0345981 A1 | 12/2016 | Demas et al. | |

(Continued)

*Primary Examiner* — Katherine H Schwiker
*Assistant Examiner* — Raihan R Khandker
(74) *Attorney, Agent, or Firm* — Diament Patent Law, P.C.; Adam Diament

(57) ABSTRACT

A tourniquet assembly is provided comprising an external band and an internal band with a first and second semi-permanent adhesive members. The external band has a first connecting member affixed thereto and a second connecting member removably connected thereto. The internal band is designed to form a loop having a circumference around a limb for constricting blood flow in the limb when the external band forms a loop when the first connecting member is attached to the second connecting member. The tourniquet assembly further comprises a tensioning member connected to the internal band and configured to apply direct tension to the internal band without applying direct tension to the external band. Herein, the circumference formed by the internal band is reduced when the tensioning member is actuated, thereby compressing the limb when the tourniquet assembly is placed around the limb, and thereby reducing blood flow to the limb.

20 Claims, 14 Drawing Sheets

(56) References Cited

U.S. PATENT DOCUMENTS

| | | |
|---|---|---|
| 2017/0265590 A1 | 9/2017 | Burns et al. |
| 2020/0096289 A1* | 3/2020 | Fischer ................. F41C 33/046 |
| 2021/0085335 A1* | 3/2021 | Dahl .................. A61B 17/1322 |
| 2021/0137252 A1* | 5/2021 | Knudsen ............... F41C 33/046 |

* cited by examiner

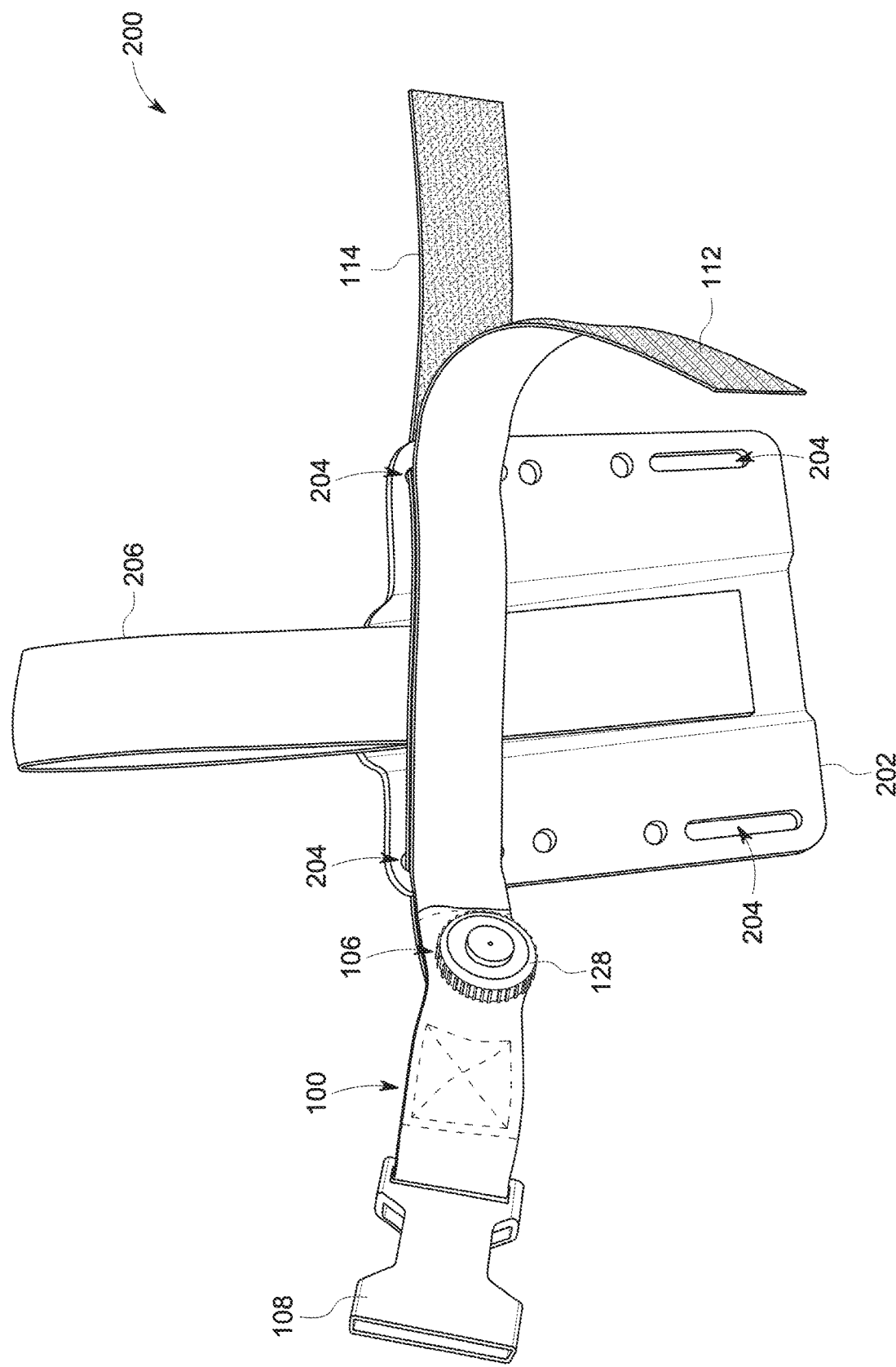

HOLSTER AND TOURNIQUET DEVICE AND METHOD OF USE

CROSS-REFERENCE TO RELATED APPLICATIONS

This application claims benefit of U.S. Provisional Patent Application No. 62/879,530, entitled "Holster and Tourniquet Device and Method of Use," filed Jul. 28, 2019, to Watts, the contents of which are incorporated by reference in its entirety.

FEDERALLY SPONSORED RESEARCH OR DEVELOPMENT

None.

FIELD OF THE DISCLOSURE

The present invention relates to a tourniquet, and more particularly to tourniquets integrated with a load bearing strap.

BACKGROUND OF THE INVENTION

Gear straps are commonly used to secure items, especially in police, military, first and responders, where equipment must be secured to the body. One type of gear strap is a strap to secure a holster to a leg. Body armor and gear backs use straps, buckles, Velcro®, hook and loop tape, and other attachment means to attached devices and tools to clothing. The same professions and activities where gear straps are necessary, tourniquets are also necessary.

For example, police officers and military personnel need to secure holsters to their body, but should also be prepared to stop bleeding, and must do so quickly. Generally, for this purpose, tourniquets are used that can control venous and arterial circulation to extremities.

There are many types of tourniquets that can be used in the field. Tourniquets that use ratcheting mechanisms are well known in the art, such as U.S. Pat. No. 8,424,168 to Soderberg et al., and U.S. Pat. No. 7,954,204 to Hammerslag et al., which use a reel system. Trauma management kits using tourniquets have also been previously described, such as U.S. Pat. No. 9,333,129 to Catrone. U.S. Pat. No. 10,492,568 to Burns et al. discloses devices and methods for tensioning apparel and other items and U.S. Pat. No. 7,981,135 discloses a garment with affixed tourniquet. Compression devices using buckles have also been described, such as that described in U.S. Patent App. Pub. No. 2016/0345981. All patent and non-patent literature cited in the entirety of this patent application are each incorporated by reference in their entireties for all purposes.

Some emergency tourniquets are integrated into gear straps to facilitate easy and quick application to stop blood flow from a limb prior to more intensive hospital care. However, gear straps, by themselves, do not function well as tourniquet device for several reasons, including the amount of time it would take to remove the gear strap from the supported gear and reapply the strap as a tourniquet. For example, tourniquets that merely use a reel-based system, and other tourniquets, have difficulty maintaining circumferential pressure if the tourniquet is also being used as a gear strap. It is to be noted that the method of wearing a tourniquet is important since the fact that the wearer has existing gear need to be considered.

Due to at least the above described shortcoming there remains a continuing need for improved gear straps and tourniquets.

BRIEF SUMMARY OF THE PRESENT INVENTION

The invention is for a tourniquet assembly that can function both as a load bearing device to secure gear to a person, as well as function as a tourniquet to slow blood flow through a limb.

In an aspect, a tourniquet assembly is provided. The tourniquet assembly comprises an external band having a proximal end, a distal end, an inner surface, and an outer surface. The inner surface of the external band includes a first semi-permanent adhesive member. The external band has a first connecting member affixed to the proximal end of the external band. The tourniquet assembly also comprises an internal band having a proximal end, a distal end, an inner surface, and an outer surface. The internal band is adapted for constricting blood flow in a limb. The outer surface of the internal band includes a second semi-permanent adhesive member adapted to adhere to the first semi-permanent adhesive member along a length of the external band, whereby the first and second semi-permanent adhesive members can easily be pulled apart and adhered together numerous times without substantial loss of adhesive properties. The internal band is designed to form a loop having a circumference around a limb when the internal band is placed around the limb. The tourniquet assembly further comprises a tensioning member connected to the internal band and configured to apply direct tension to the internal band without applying direct tension to the external band. Herein, the circumference formed by the internal band is reduced when the tensioning member is actuated, thereby compressing the limb when the tourniquet assembly is placed around the limb, and thereby reducing blood flow to the limb. Further, the internal band at least partially separates from the external band when the tensioning member is actuated due to direct tension being applied to the internal band from the tensioning member, but little or no direct tension being applied to the external band.

In one or more embodiments, the external band and the internal band are attached together at the respective proximal ends.

In one or more embodiments, the external band and the internal band are sewn together along a portion of lengths thereof at the respective proximal ends.

In one or more embodiments, the first connecting member is affixed to the proximal ends of the external band and the internal band.

In one or more embodiments, there is and a second connecting member removably connected to the distal end of the external band, wherein the external band forms a loop when the first connecting member is attached to the second connecting member. The external band and the internal band are adapted to be adhered together at least at the respective distal ends, with the second connecting member connected thereto, to allow for the tourniquet assembly to form a loop when the first connecting member is attached to the second connecting member.

In one or more embodiments, the external band and the internal band are adapted to be pulled apart at least at the respective distal ends, with the second connecting member disconnected therefrom, to allow for the tourniquet assembly, at the distal ends of the external band and the internal band, to guide through one or more channels in a plate of a holster-tourniquet equipment.

In one or more embodiments, the external band and the internal band are adapted to be adhered back together at least at the respective distal ends, with the second connecting member connected thereto, after guiding of the tourniquet assembly through one or more channels in the plate of the holster-tourniquet equipment, to affix the tourniquet assembly in the holster-tourniquet equipment.

In one or more embodiments, the second connecting member includes at least two slots formed therein. The external band and the internal band at the distal ends thereof, when adhered back together, are adapted to pass through the at least two slots in the second connecting member to adjust a circumference of the loop formed by the external band when the first connecting member is attached to the second connecting member.

In one or more embodiments, the tensioning member includes a dial configured to be rotated to cause the internal band to uptake for applying direct tension to the internal band without applying direct tension to the external band.

In one or more embodiments, the tensioning member includes a windlass configured to be turned to cause the internal band to uptake for applying direct tension to the internal band without applying direct tension to the external band.

In one or more embodiments, the tensioning member is placed over the outer surface of the external band for quick access by a user. The external band includes a grommet inserted into a hole therein to allow for the tensioning member to be connected to the internal band and apply direct tension thereto without applying direct tension to the external band.

In one or more embodiments, the inner surface of the internal band includes a protective covering.

In one or more embodiments, the first and second semi-permanent adhesive members are hook-and-loop based fasteners.

In one or more embodiments, the first connecting member is one of a male buckle part and a female buckle part, and the second connecting member is other of the male buckle part and the female buckle part, to allow for the first connecting member and the second connecting member to attach with each other.

In another aspect, an apparatus is provided (that may be a holster-tourniquet equipment). The apparatus includes a plate having one or more channels formed therein. The apparatus further includes a tourniquet assembly. The tourniquet assembly comprises an external band having a proximal end, a distal end, an inner surface, and an outer surface. The inner surface of the external band includes a first semi-permanent adhesive member. The external band has a first connecting member affixed to the proximal end of the external band. The tourniquet assembly also comprises an internal band having a proximal end, a distal end, an inner surface, and an outer surface. The internal band is adapted for constricting blood flow in a limb. The outer surface of the internal band includes a second semi-permanent adhesive member adapted to adhere to the first semi-permanent adhesive member along a length of the external band, whereby the first and second semi-permanent adhesive members can easily be pulled apart and adhered together numerous times without substantial loss of adhesive properties. The internal band is designed to form a loop having a circumference around a limb when the internal band is placed around the limb. The external band and the internal band are adapted to be pulled apart at least from the respective distal ends, to allow for the tourniquet assembly, at the distal end of the external band to guide through the one or more channels in the plate of the holster-tourniquet equipment. The tourniquet assembly further comprises a tensioning member connected to the internal band and configured to apply direct tension to the internal band without applying direct tension to the external band. Herein, the circumference formed by the internal band is reduced when the tensioning member is actuated, thereby compressing the limb when the tourniquet assembly is placed around the limb, and thereby reducing blood flow to the limb. Further, the internal band at least partially separates from the external band when the tensioning member is actuated due to direct tension being applied to the internal band from the tensioning member, but no direct tension being applied to the external band.

In one or more embodiments, the plate is adapted to be arranged on a thigh of a leg of a user such that the internal band of the tourniquet assembly forms a loop around the thigh of the leg of the user, and wherein the plate includes means for receiving a gun holster thereon, thereby forming a holster-tourniquet equipment.

In one or more embodiments, the plate is in the form of a shoulder pad adapted to be arranged on an upper arm of a user such that the internal band of the tourniquet assembly forms a loop around the upper arm of the user. The one or more channels are in the form of loops formed on the shoulder pad.

In one or more embodiments, a second connecting member removably connected to the distal end of the external band, wherein the external band forms a loop when the first connecting member is attached to the second connecting member. The external band and the internal band are adapted to be adhered back together at least at the respective distal ends, with the second connecting member connected thereto, after guiding of the tourniquet assembly through one or more channels in the plate of the holster-tourniquet equipment, to affix the tourniquet assembly in the holster-tourniquet equipment.

In one or more embodiments, the second connecting member includes at least two slots formed therein, and wherein the external band and the internal band at the distal ends thereof, when adhered back together, are adapted to pass through the at least two slots in the second connecting member to adjust a circumference of the loop formed by the external band when the first connecting member is attached to the second connecting member.

In one or more embodiments, the second connecting member includes at least two slots formed therein. The external band and the internal band at the distal ends thereof, when adhered back together, are adapted to pass through the at least two slots in the second connecting member to adjust a circumference of the loop formed by the external band when the first connecting member is attached to the second connecting member.

BRIEF DESCRIPTION OF THE DRAWINGS

For a more complete understanding of example embodiments of the present disclosure, reference is now made to the following descriptions taken in connection with the accompanying drawings in which:

FIG. 5A is front perspective of a holster-tourniquet equipment with the external band of the tourniquet assembly of FIG. 1 guided through channels in a plate thereof, in accordance with an embodiment of the present disclosure;

DETAILED DESCRIPTION OF EMBODIMENTS

Figure 1:
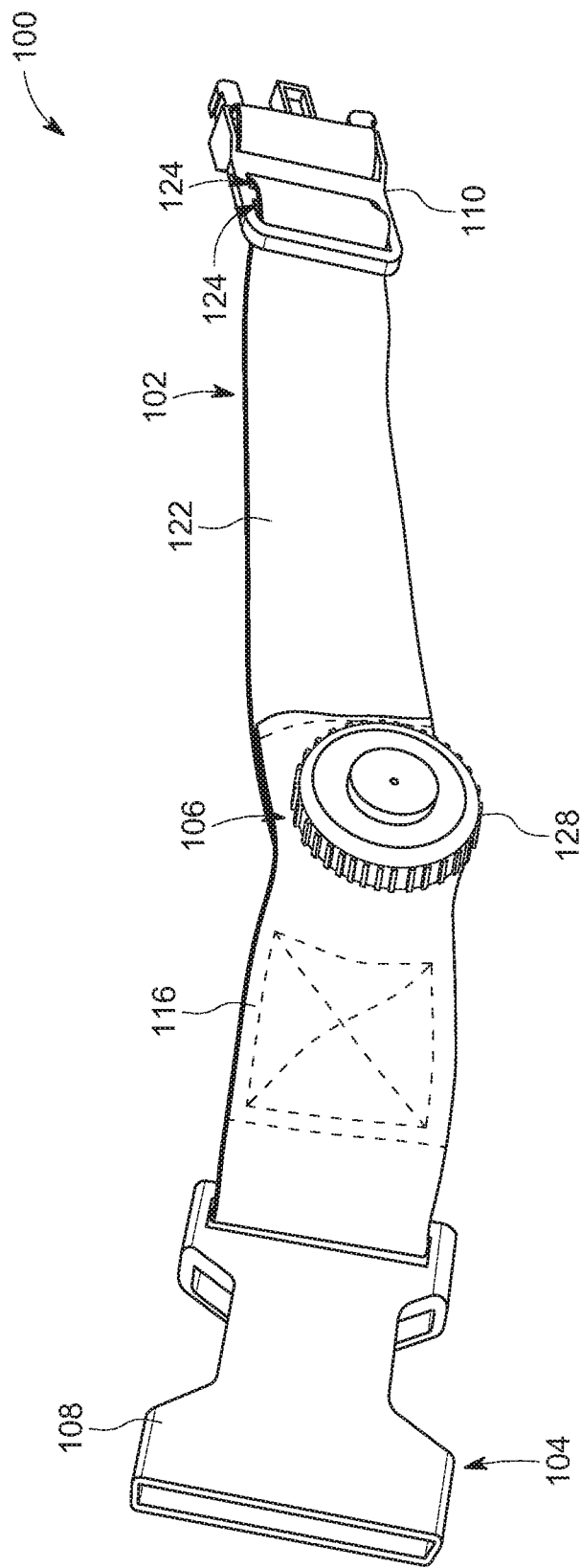
FIG. 1 is a front perspective view of a tourniquet assembly, in accordance with an embodiment of the present disclosure.

The invention now will be described more fully hereinafter with reference to the accompanying drawings, in which embodiments of the invention are shown. This invention may however be embodied in many different forms and should not be construed as limited to the embodiments set forth herein. Rather, these embodiments are provided so that this disclosure will be thorough and complete, and will fully convey the scope of the invention to those skilled in the art.

It will be understood that when an element is referred to as being "on" another element, it can be directly on the other element or intervening elements may be present therebetween. As used herein, the term "and/or" includes any and all combinations of one or more of the associated listed items.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section.

It will be understood that the elements, components, regions, layers and sections depicted in the figures are not necessarily drawn to scale.

The terminology used herein is for the purpose of describing particular embodiments only, and is not intended to be limiting of the invention. As used herein, the singular forms "a," "an," and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom," "upper" or "top," "left" or "right," "above" or "below," "front" or "rear," may be used herein to describe one element's relationship to another element as illustrated in the Figures. It will be understood that relative terms are intended to encompass different orientations of the device in addition to the orientation depicted in the Figures.

Unless otherwise defined, all terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing. The invention illustratively disclosed herein suitably may be practiced in the absence of any elements that are not specifically disclosed herein.

The embodiments describe generally relate to devices that can be used as for equipment, an equipment holster, equipment bracket, equipment bag, body armor strap, arm strap, leg strap, thigh strap, body armor/body armor carrier strap, emergency medical equipment, hunting equipment, gun holster, or gun holster strap with an integrated adjustment mechanism and/or integrated tourniquet that can be used from an "in use" or "donned" position. In particular an advantage of the integrated tourniquet is that the user does not need to remove equipment or straps holding equipment because integrated tourniquet has both a load bearing portion and a tourniquet portion that a user can immediate apply the tensioning tourniquet portion without removing the load bearing portion. Since time is of utmost importance when applying a tourniquet, due to blood loss, the present embodiments will save lives by decreasing the amount of time it takes to apply a tourniquet when wearing other gear, such as a firearm, taser, body armor, gear bags, and the like. Embodiments described can use standard straps, buckles, Velcro, hood and loop tape. The integrated adjustment mechanism on the tourniquet can be tightened or loosed while it is donned and in place. The assembly allows the user to make quick adjustments to the donned gear and/or apply the integrated tourniquet without having to remove gear or re-route straps or buckles. Large versions of the assembly can be used for the upper thighs and heavier applications, while smaller versions of the assembly can be used for the upper arms or lighter applications.

The tension can be created with an internal band, wire, or fabric, that runs the sufficient length of the strap and is anchored to the buckles, Velcro, hook and fiber tape, or other attachment mechanism. On the strap is a ratcheting mechanism or tourniquet tightening device capable of operation while equipment is donned and in place. An example of the product use would be to replace the top strap on a drop leg gun holster which secures around an operator's upper thigh. As the operator moves and gear adjusts the strap becomes loose. With the gear strap the operator will be able to quickly reach down and turn the fine adjustment mechanism or tourniquet tightening device the desired amount. If the same operator sustains a gunshot wound to the lower leg, the device can be tightened further to slow or stop blood flow.

In addition, the present embodiments are useful for when a user encounters a situation where gear needs to be tightened but there no time to unbuckle or adjust straps in the traditional manner. The present embodiment has an internal band that can lie directly on or over clothing (or the body), while an external band can route through a gun/gear/armor holster. This arrangement of bands allows the internal band lying against the clothing or body to create and maintain the circumferential pressure necessary to stop or slow blood flow. Because the external band routes through the gear/holster/carrier is joined to the tourniquet via an attachment mechanism such a hook and loop fastening or Velcro.

Figure 2:
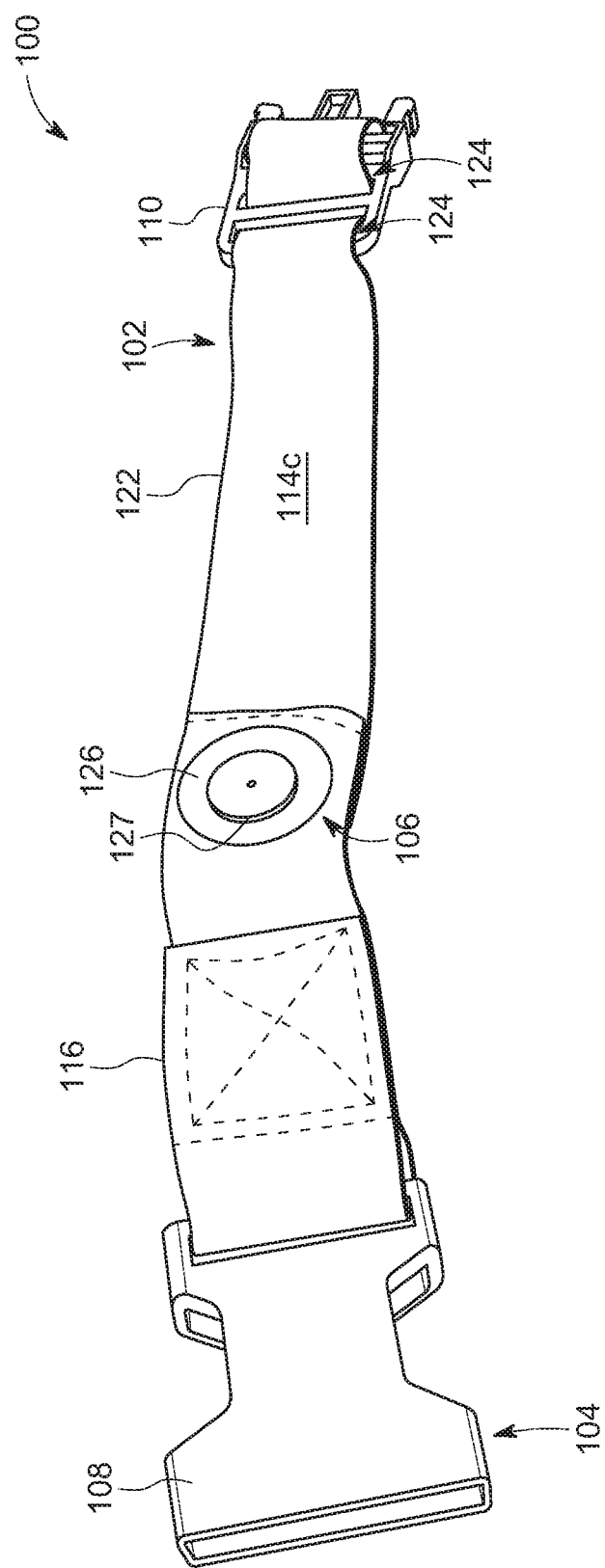
FIG. 2 is a rear perspective view of the tourniquet assembly of FIG. 1.

Turning to the Figures, FIGS. 1-2 depict a tourniquet assembly 100, in accordance with an embodiment of the present disclosure. As depicted, the tourniquet assembly 100 includes a strap portion 102, a locking arrangement 104 and a tensioning member 106. The strap portion 102 acts as a load bearing member in the tourniquet assembly 100. The strap portion 102 is generally in the form of an elongate member which may loop around an object to be wrapped around. The dimensions of the strap portion 102 are generally defined based on a size of the object to which the tourniquet assembly 100 is tied with. That is, the strap portion 102 is designed to have a sufficient length so as to be able to loop around the object to which the tourniquet assembly 100 is to be wrapped around. Further, the strap portion 102 has a width sufficient enough to make application of the tourniquet assembly 100 tolerable for a period during which an injured person is transported. Furthermore, the strap portion 102 has a thickness sufficient enough to provide the required load bearing capacity yet be able to engage with the object (e.g., pass through channels available in the object, as discussed later in the description in more detail).

In one embodiment, the strap 102 (either the strap 102 as a whole, the external band 112, and/or internal band 114) is approximately 1.5 inches. The length of the strap 102 depends on the application (such as use on an arm or a leg). For arm (shoulder pad) versions, the strap 102 may be 10 inches, 15 inches, or 20 inches, or any value in between, and may be larger or smaller to accommodate the circumference of the user's upper arm. For leg versions, the strap 102 may be 15 inches, 20 inches, 25 inches, 30 inches, 35 inches, values in between, larger or smaller to accommodate the larger circumference of a human thigh compared to a human upper arm. Ranges of dimensions ±5%, 10%, 25%, 50%, 75% or 100% may be used without detracting from the spirit and scope of the invention.

As depicted, the locking arrangement 104 includes a first connecting member 108 and a second connecting member 110. In one or more embodiments, the locking arrangement 104 is in the form of a buckle assembly that releasably connects the first connecting member 108 and the second connecting member 110. The first connecting member 108 and the second connecting member 110 may be buckle parts with single direction locking mechanisms. In the illustrated examples, the first connecting member 108 is shown as the female bucket part and the second connecting member 110 is shown as the male bucket part. However, it may be appreciated that the first connecting member 108 may be the male bucket part and the second connecting member 110 may be the female bucket part without departing from the scope and spirit of the present disclosure. In one or more examples, each of the first connecting member 108 and the second connecting member 110 may include a rigid projection configured to prevent rotation of the corresponding buckle part relative to the strap portion 102 in the tourniquet assembly 100. Such locking arrangement 104 allows for the tourniquet assembly 100 to form a loop when the first connecting member 108 is attached to the second connecting member 110, which is required for its application as discussed in the proceeding paragraphs.

Figure 3:
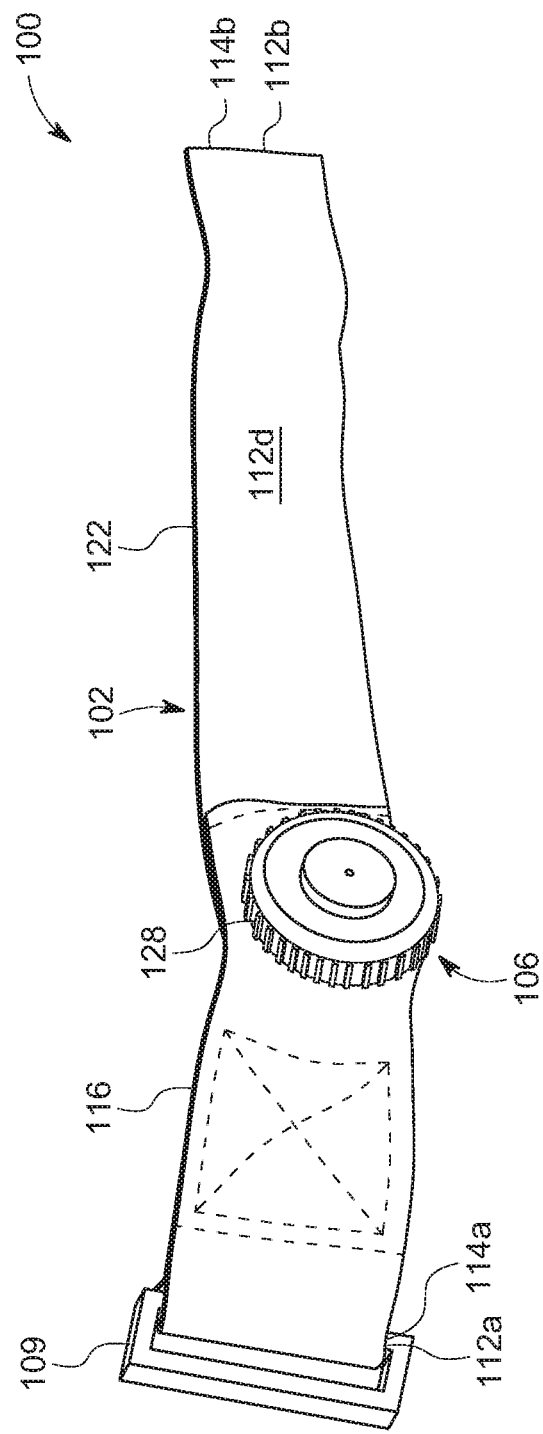
FIG. 3 is a front perspective view of a tourniquet assembly having a d-ring attachment member instead of a buckle.
Figure 4:
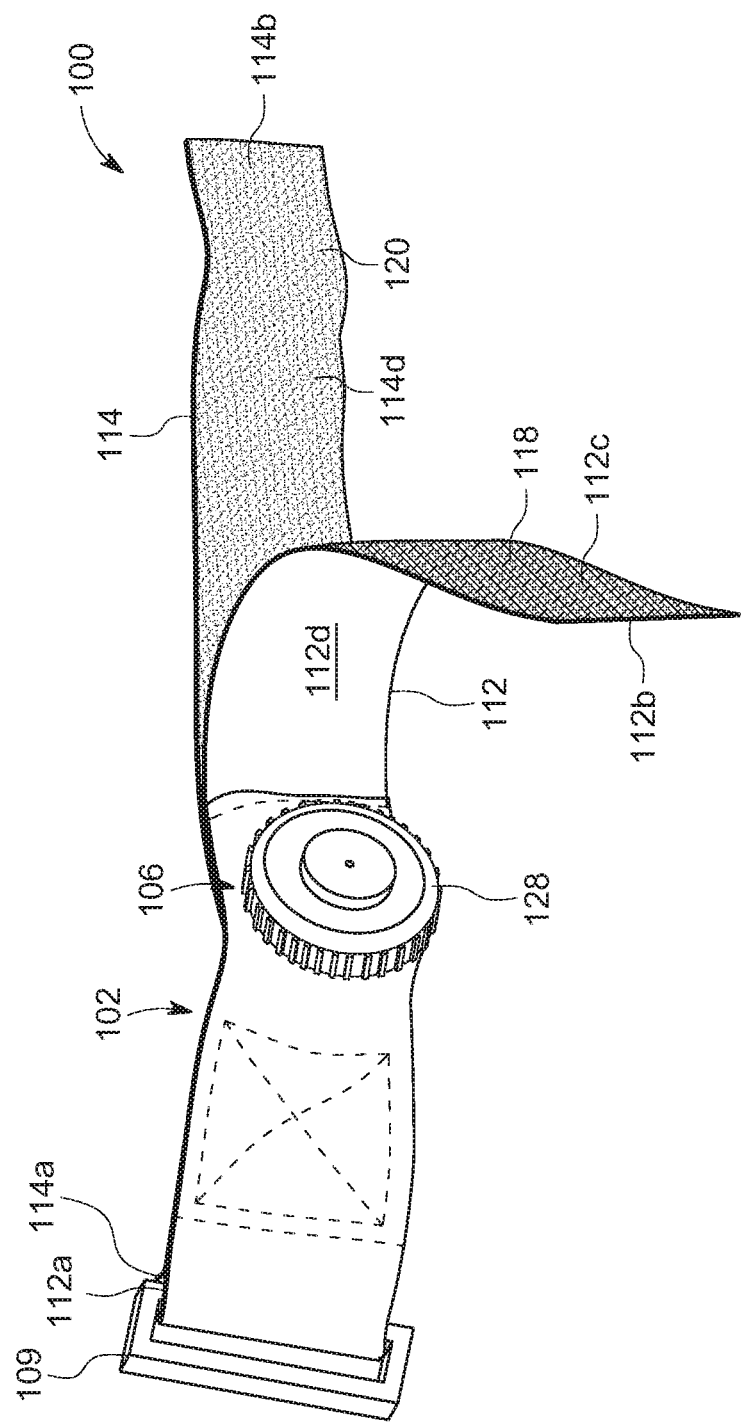
FIG. 4 is a front perspective view of the tourniquet assembly of FIG. 3 with an external band and an internal band pulled apart therein.

Referring to FIGS. 3-4, as depicted, the strap portion 102 of the tourniquet assembly 100 includes an external band 112 and an internal band 114. The external band 112 and the internal band 114 are elongate members extending together to form the strap portion 102. The external band 112 has a proximal end 112a, a distal end 112b, an inner surface 112c, and an outer surface 112d. Similarly, the internal band 114 has a proximal end 114a, a distal end 114b, an inner surface 114d (as shown in FIG. 2), and an outer surface 114c. Herein, the strap portion 102 is formed such that the inner surface 112c of the external band 112 is facing the inner surface 114d of the internal band 114. The external band 112 and the internal band 114 are attached together at the respective proximal ends 112a, 114a. In an embodiment, the external band 112 and the internal band 114 are sewn together along an affixed portion 116 of lengths thereof at the respective proximal ends 112a, 114a. This way the external band 112 and the internal band 114 stay joined at least along the affixed portion 116 of lengths thereof, in the strap portion 102. FIGS. 3 and 4 show an embodiment where instead of a buckle, used to connect the proximal ends of the strap 112a, 114a, a D-ring 109 is used. In this type of embodiment, which may be used in many other types of embodiments in lieu of buckles, the distal ends 112b, 114b of the strap be pulled through the D-ring 109 and secured over itself (such as by the Velcro attachment). Other types of attachment means may also be used without detracting from the scope and spirit of the invention.

According to the embodiments of the present disclosure, as better shown in FIG. 4, the inner surface 112c of the external band 112 includes a first semi-permanent adhesive member 118. Similarly, the inner surface 114d of the internal band 114 includes a second semi-permanent adhesive member 120. As aforementioned, the strap portion 102 is formed such that the inner surface 112c of the external band 112 is facing the inner surface 114d of the internal band 114, thus the second semi-permanent adhesive member 120 is adapted to adhere to the first semi-permanent adhesive member 118 along a length 122 of the external band 112, other than the affixed portion 116 of length of the external band 112. The first and second semi-permanent adhesive members 118, 120 can easily be pulled apart and adhered together numerous times without substantial loss of adhesive properties.

In an embodiment, as depicted, the first and second semi-permanent adhesive members 118, 120 are hook-and-loop based fasteners. Such fastening arrangements are well known in the art and thus has not been described herein. In alternate examples, the first and second semi-permanent adhesive members 118, 120 may be snaps, clips, popper buttons, metal hooks and/or another suitable attachment mechanism that can releasably secure the external band 112 and the internal band 114 without any limitations.

In the present embodiments, the first connecting member 108 is affixed to the proximal end 112a of the external band 112, and the second connecting member 110 is removably connected to the distal end 112b of the external band 112. As depicted, the first connecting member 108 is engaged with the affixed portion 116 of length of the external band 112, with the affixed portion 116 sewn later (as discussed) to affix the first connecting member 108 to the proximal end 112a of the external band 112. In other examples, the first connecting member 108 may be affixed to the proximal end 112a of the external band 112 using rivets or the like. It may be appreciated that the first connecting member 108 is affixed to the proximal ends 112a, 114a of the external band 112 as well as the internal band 114, as the external band 112 and the internal band 114 are joined together at the respective proximal ends 112a, 114a, along the affixed portion 116 of length of the strap portion 102.

Further, as depicted, the second connecting member 110 is engaged with the external band 112. It may be seen that the second connecting member 110, when connected, is attached with the distal ends 112b, 114b of the external band 112 as well as the internal band 114. In an embodiment, the second connecting member 110 includes at least two slots 124 formed therein. As shown in FIGS. 1-3, the second connecting member 110, in the form of a buckle part, includes two slots 124 formed therein. The external band 112 and the internal band 114 at the distal ends 112b, 114b thereof, when adhered together, are adapted to pass through the two slots 124 in the second connecting member 110 to attach the second connecting member 110 therewith. Such connection of the buckle parts with a strap is well known in the art and thus have not been described herein.

In the present embodiments, the external band 112 forms a loop when the first connecting member 108 is attached to the second connecting member 110. That is, when the strap portion 102, with the external band 112 and the internal band 114 adhered together, is arranged so that the first connecting member 108 and the second connecting member 110 are attached to each other, the strap portion 102 forms a loop. Herein, the internal band 114 is designed to form a loop having a circumference around a limb when the internal band 114 is placed around the limb. That is, when the tourniquet assembly 100 is to be worn by a user around a limb, the internal band 114 forms the loop having the circumference around the limb of the user.

Further, as discussed, the external band 112 and the internal band 114 at the distal ends 112b, 114b thereof, when adhered together, are adapted to pass through the two slots 124 in the second connecting member 110 to adjust a circumference of the loop formed by the external band 112 when the first connecting member 108 is attached to the second connecting member 110. This way changing the length of portion of the external band 112 and the internal band 114 passing through the two slots 124 from the at the distal ends 112b, 114b thereof, the circumference of the loop formed by the external band 112 (and the internal band 114) can be adjusted, and, in turn, allow the strap portion 102 to be adjusted such that the tourniquet assembly 100 fits over the limb of the user.

Further, as depicted, the tensioning member 106 is placed over the outer surface 112d of the external band for quick access by a user. In the tourniquet assembly 100, the tensioning member 106 is connected to the internal band 114. This way, the tensioning member 106 is configured to apply direct tension to the internal band 114 without applying direct tension to the external band 112. For this purpose, the external band 112 includes a hole 127 (an opening) formed therein, generally close to the proximal end 112a and in the affixed portion 116 of the length thereof. Further, the external band 112 includes a grommet 126 (as shown in FIG. 2) inserted into the hole formed therein. This allow for the tensioning member 106 to be connected to the internal band 114 and apply direct tension thereto without applying direct tension to the external band 112.

In the tourniquet assembly 100, the external band 112 and the internal band 114 can be made from woven nylon (e.g., webbing), leather, plastic, rubber, cotton, and/or another suitable material that can withstand tension forces sufficient to cut off blood flow in a limb of a user. In some examples, the outer surface 114c of the internal band 114 includes a protective covering (not shown). The protective covering may be made of any suitable water-proof and/or weather-proof material to protect the internal band 114 from damage due to exposure to the environment and for being in contact with the limb of the user. The internal band 114 is adapted for constricting blood flow in the limb. For this purpose, the internal band 114 may be in the form of a sleeve and include a wire or the like which may be wrapped around the tensioning member 106 connected thereto, so as be pulled by the tensioning member 106 when the tensioning member 106 is rotated or turned. This causes the internal band 114 to shrink in diameter, and thus apply pressure for constricting blood flow in the limb.

In an embodiment, as depicted in FIGS. 1-9, the tensioning member 106 includes a dial 128 configured to be rotated to cause the internal band 114 to uptake for applying direct tension to the internal band 114 without applying direct tension to the external band 112. Such tensioning member 106 is also known as BOA® system in the trade and is known to be used as a constricting device. Generally, in such tensioning member 106, the dial 128 also act as a locking button to keep the strap portion 102 tensioned or constricted when locked, and allow for further tensioning or releasing of tension by rotating when unlocked.

Figure 9:
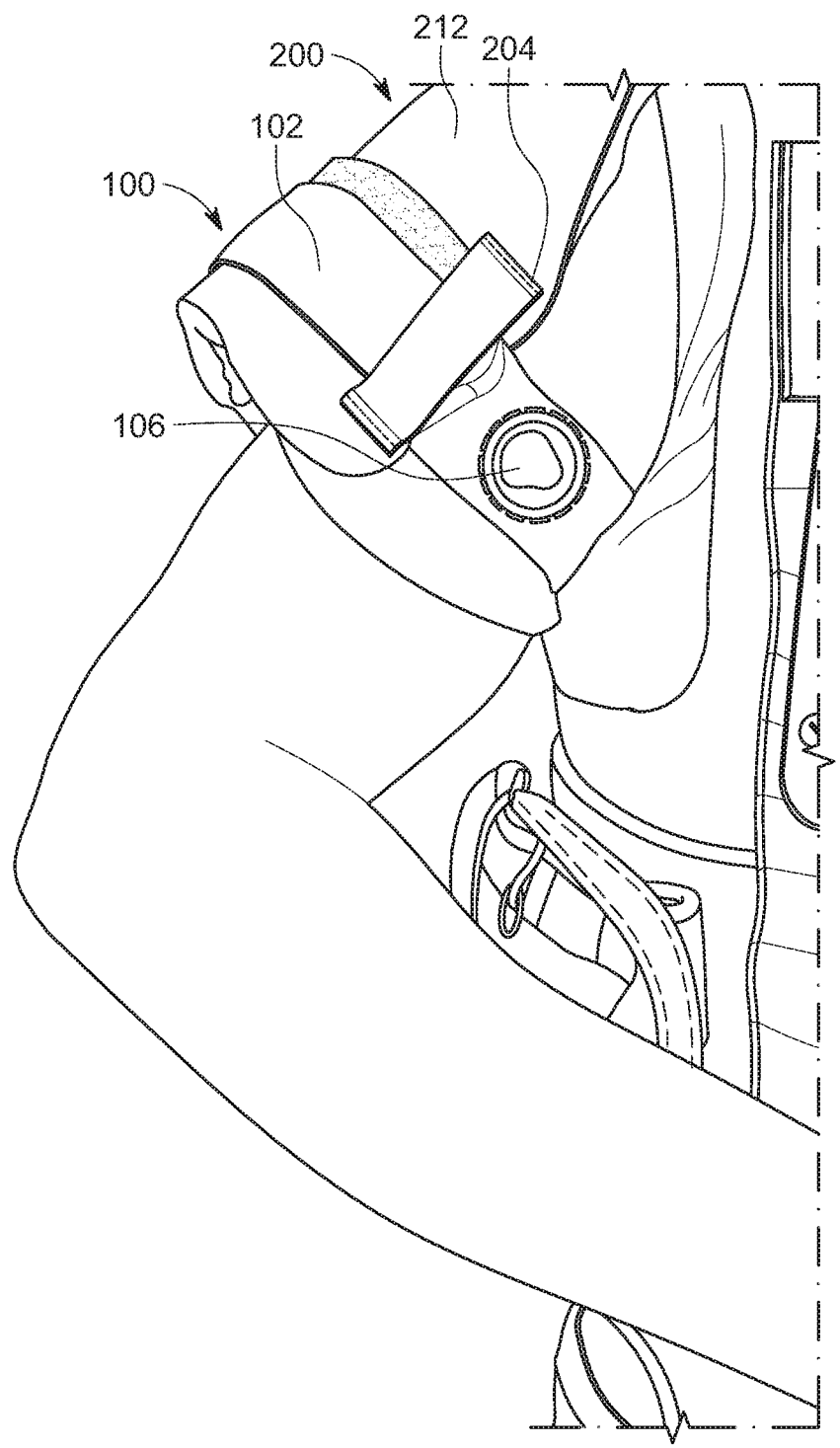
FIG. 9 is an environmental view of the holster-tourniquet equipment of FIGS. 5A-5B being used with a shoulder pad arranged on an upper arm of a user.
Figure 10:
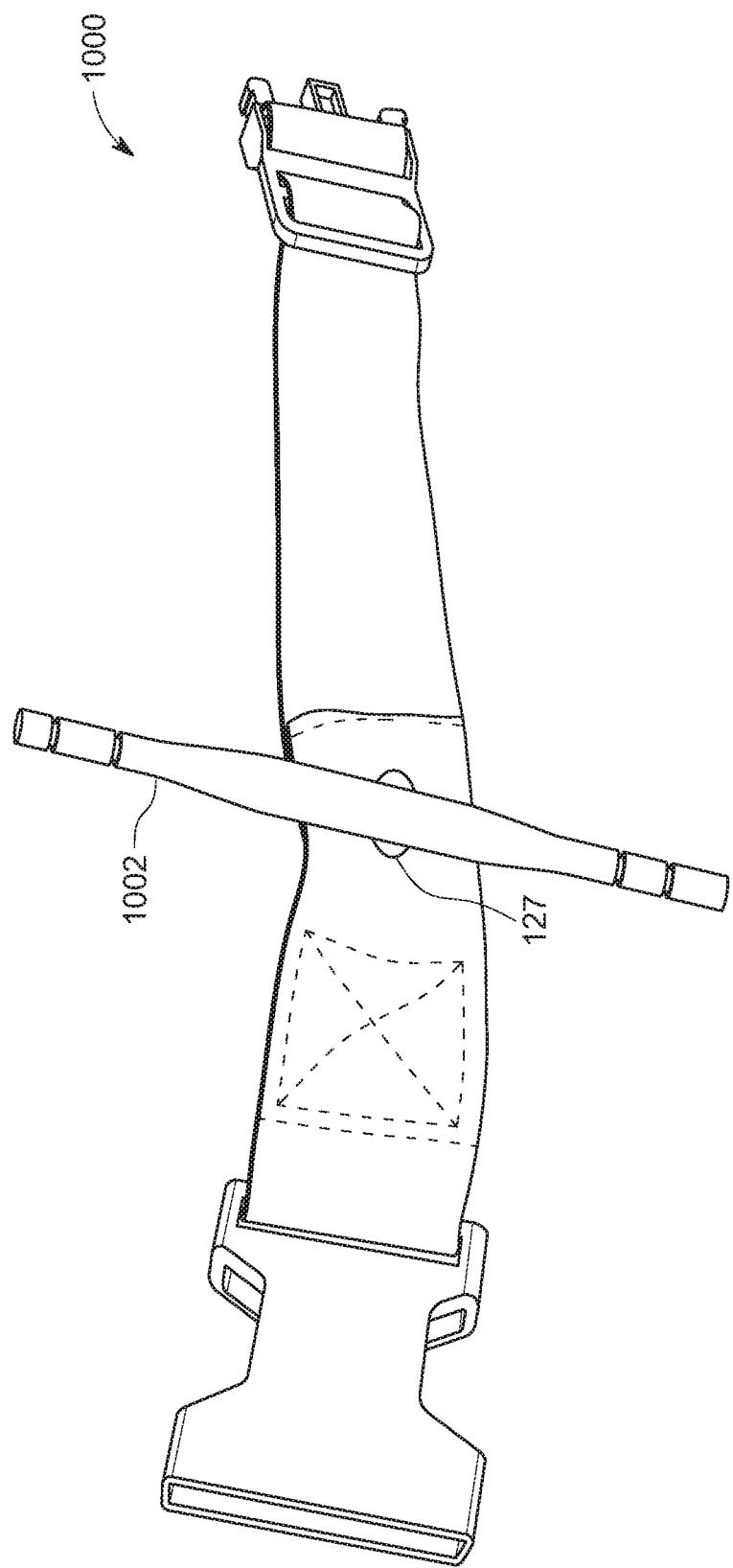
FIG. 10 is a rear perspective view of a tourniquet assembly, in accordance with another embodiment of the present disclosure.
Figure 11:
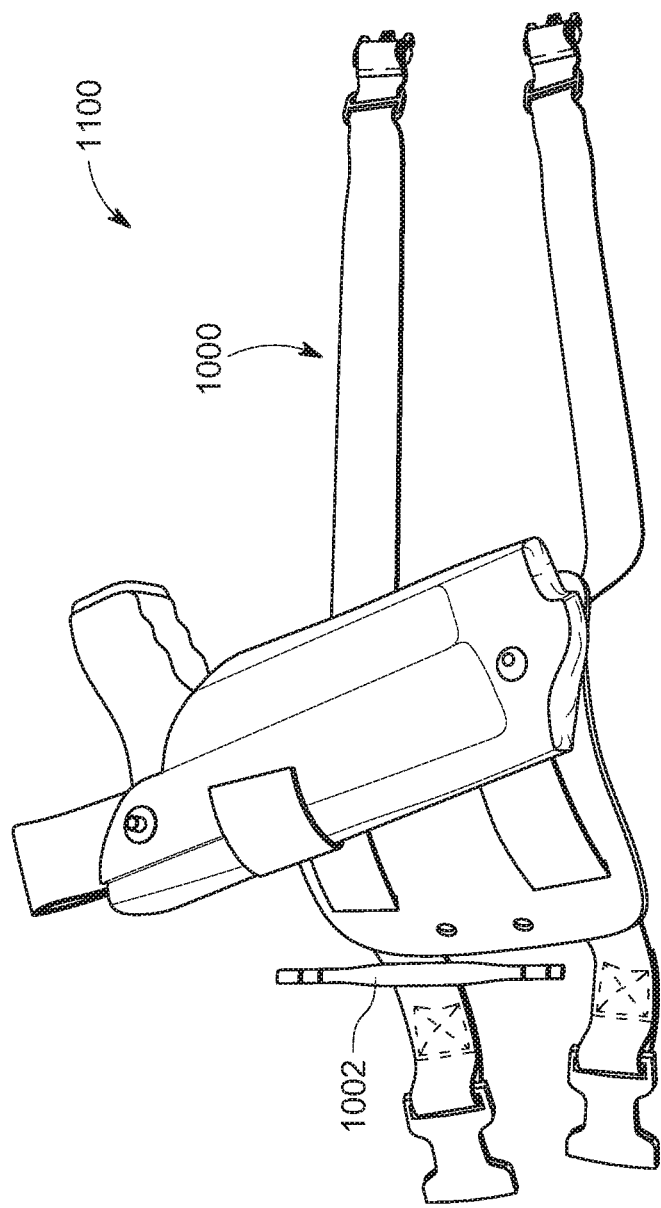
FIG. 11 is a front perspective view of a holster-tourniquet equipment with the tourniquet assembly of FIG. 10; and, FIG. 12 is an environmental view of the holster-tourniquet equipment of FIG. 11 being used as with gun holster arranged on a thigh of a leg of a user.
Figure 12:
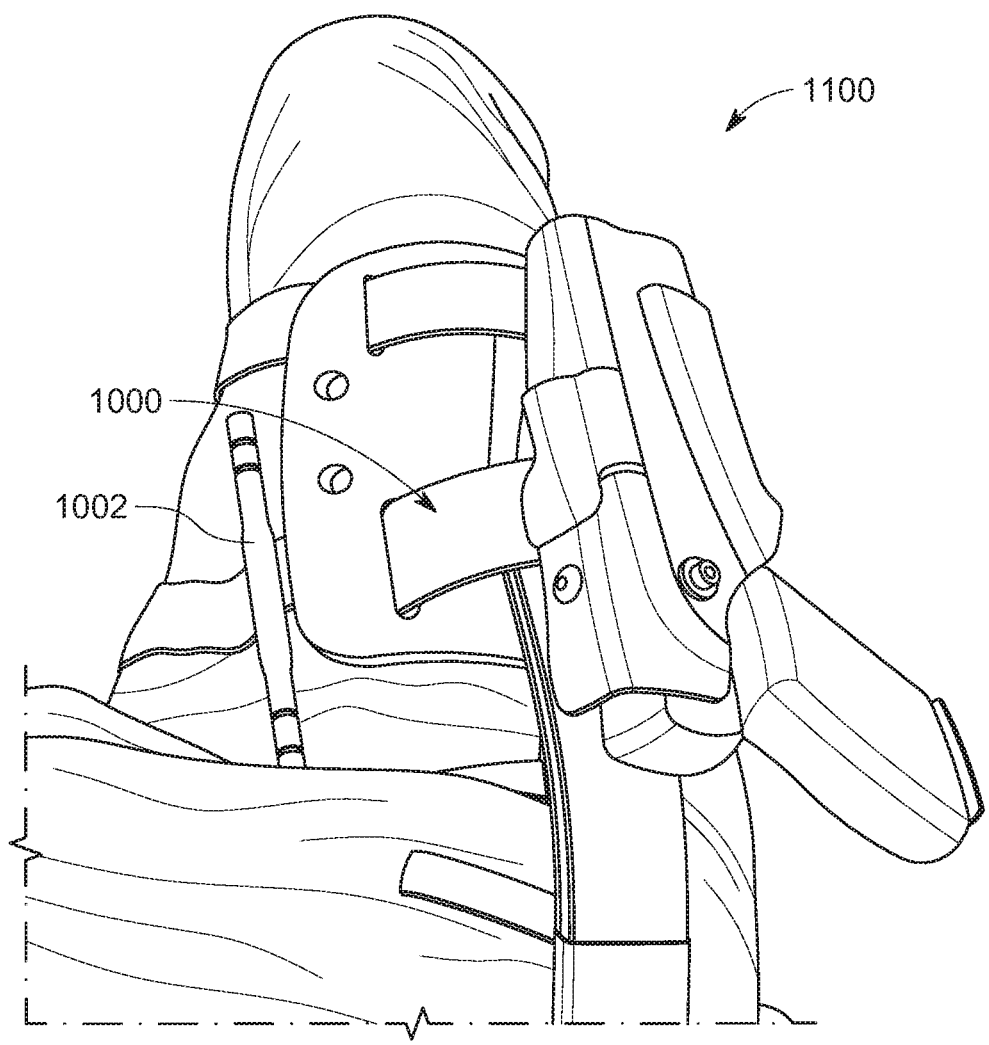

In another embodiment, as depicted in FIGS. 10-12, the tensioning member (which may be a windlass) is 1002 configured to be turned to cause the internal band 114 to uptake for applying direct tension to the internal band 114 without applying direct tension to the external band 112. As best shown in FIG. 9, the windlass 1002 is in the form of a bar engaged with the internal band 114. Such tensioning member 106 is also known as Combat Application Tourniquet, CAT®, system in the art and is known to be used as a constricting device. In one or more examples, such tensioning member 106 may also include a clamp/bracket arrangement (not shown) formed on the external band 112 to lock the windlass 1002 therewith, to prevent unintentional turning thereof. A clamp or bracket to secure the rotated windlass 1002 is well-known in the trade.

Figure 5B:
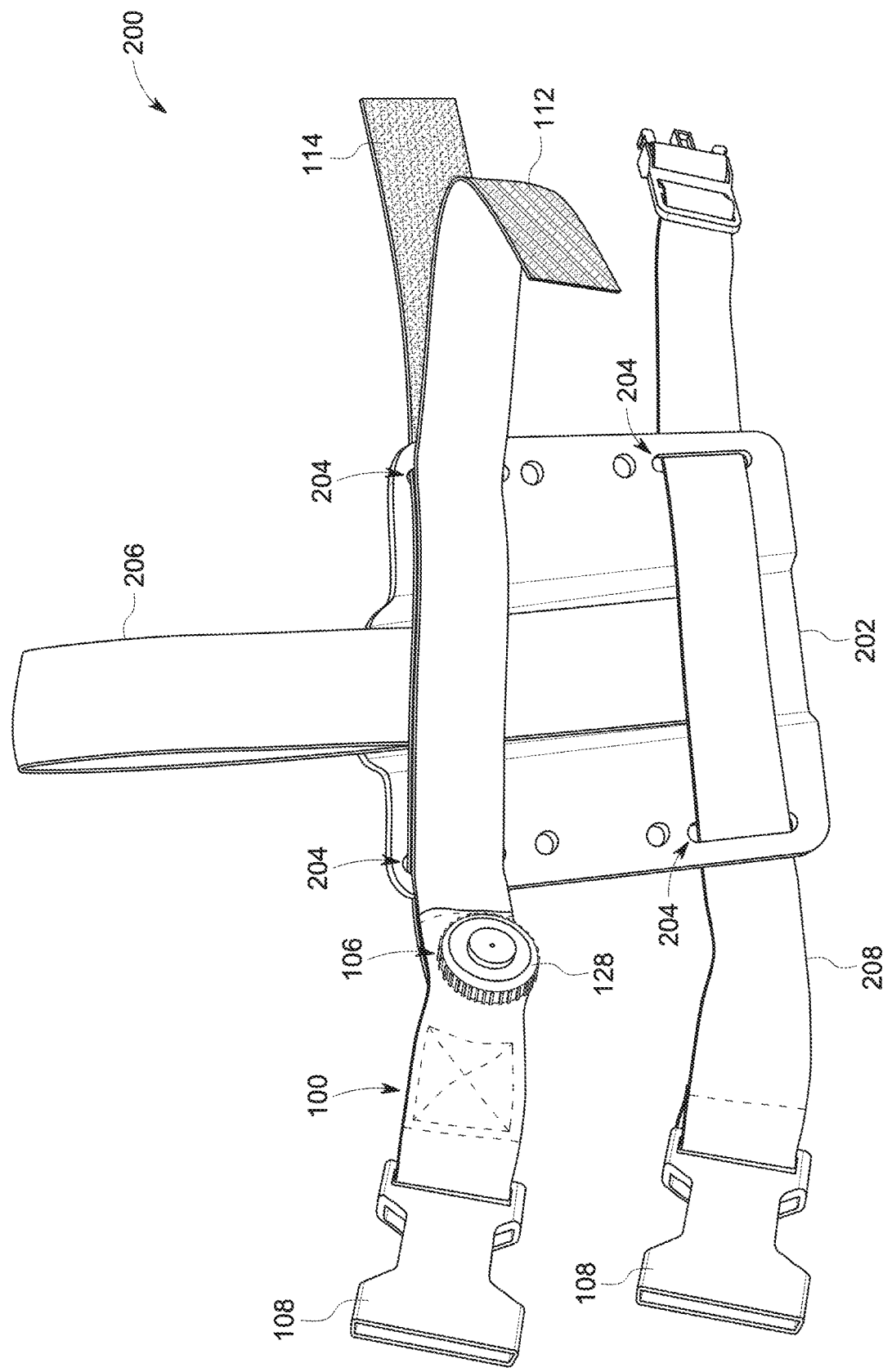
FIG. 5B is a front perspective view of the holster-tourniquet equipment with the tourniquet assembly of FIG. 1 affixed therewith.

FIGS. 5A-5B depict a holster-tourniquet equipment 200, in accordance with an embodiment of the present disclosure.

Figure 8:
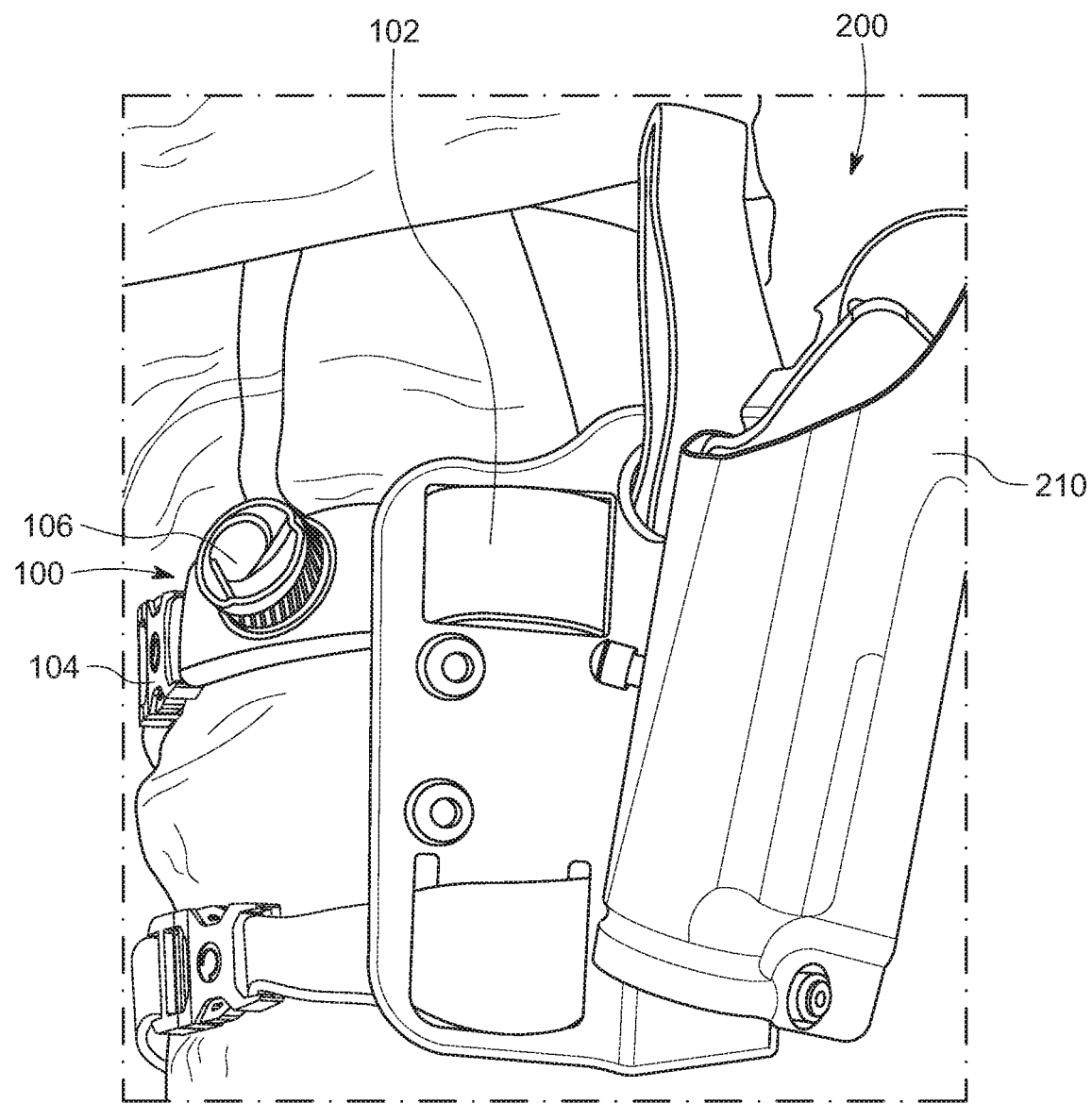
FIG. 8 is an environmental view holster-tourniquet equipment of FIGS. 5A-5B being used as with gun holster arranged on a thigh of a leg of a user.

The holster-tourniquet equipment 200 enables the tourniquet assembly 100 to be integrated with holster support means to be worn by a user at select locations (e.g., upper limb portions). For example, the holster-tourniquet equipment 200 may be in the form of gun holster (as shown in FIG. 8) or a shoulder pad (as shown in FIG. 9). The holster-tourniquet equipment 200 can be integrated into clothing and encircle an upper thigh portion in each leg of a pair of pants of the user. In an emergency, the user could directly employ the tourniquet by using the tensioning member 106 in the tourniquet assembly 100 on his or her leg. Thus, the holster-tourniquet equipment 200 can be conveniently donned around a limb for quick application in emergencies.

As depicted in FIGS. 5A-5B, the holster-tourniquet equipment 200, generally, includes a plate 202. The plate 202 acts as a support means for arranging various components in the holster-tourniquet equipment 200. In the illustrated examples, the plate 202 is shown to be of generally rectangular shape; however, the plate 202 may have any suitable shape depending on the application of the holster-tourniquet equipment 200. Generally, the plate 202 may have an arc-shaped cross-section profile to conform to shape of the limb of the user to which the holster-tourniquet equipment 200 is arranged on. For the purposes of the present disclosure, the plate 202 includes one or more channels 204 formed therein. The channels 204 are in the form of passageways formed in the plate 202. The channels 204 may be arranged in any suitable form, like parallel or staggered form depending on the requirement. The holster-tourniquet equipment 200 may further include a belt loop 206. The belt loop 206 is adapted for connecting and supporting the holster-tourniquet equipment 200 with a garment worn by, such as a belt of a pant encircling the waist of, the user.

The tourniquet assembly 100 is connected to the holster-tourniquet equipment 200 to enable the applications as discussed. For this purpose, as depicted in FIGS. 5A-5B, the external band 112 and the internal band 114 are adapted to be pulled apart at least at the respective distal ends 112b, 114b, with the second connecting member 110 disconnected therefrom, to allow for the tourniquet assembly 100, at the distal ends 112b, 114b of the external band 112 and the internal band 114, to guide through the one or more channels 204 in the plate 202 of the holster-tourniquet equipment 200. Further, the external band 112 and the internal band 114 are adapted to be adhered back together at least at the respective distal ends 112b, 114b, with the second connecting member 110 connected thereto, after guiding of the tourniquet assembly 100 through the one or more channels 204 in the plate 202 of the holster-tourniquet equipment 200, to affix the tourniquet assembly 100 in the holster-tourniquet equipment 200. In other words, first, the second connecting member 110 is disconnected by removing the strap portion 102 from the slots 124 therein. Then, the strap portion 102 from the distal ends 112b, 114b is guided through the channels 204 in the plate 202. Thereafter, the second connecting member 110 is again connected to the strap portion 102 by passing the strap portion 102 through the slots 124 therein. Finally, the external band 112 and the internal band 114 are adhered back together to affix the tourniquet assembly 100 in the holster-tourniquet equipment 200.

In the holster-tourniquet equipment 200, the external band 112 and the internal band 114 are adapted to be adhered together at least at the respective distal ends 112b, 114b, with the second connecting member 110 connected thereto, to allow for the tourniquet assembly 100 to form a loop when the first connecting member 108 is attached to the second connecting member 110. This way the holster-tourniquet equipment 200 could be used as an integrated gear means for supporting various accessories while also being applicable to be used as an emergency tourniquet. In some examples, as depicted in FIG. 5B, the holster-tourniquet equipment 200 further includes a second strap 208 with self-locking arrangement to be able to form a loop, for example, for encircling a limb of a user or the like.

Figure 6A:
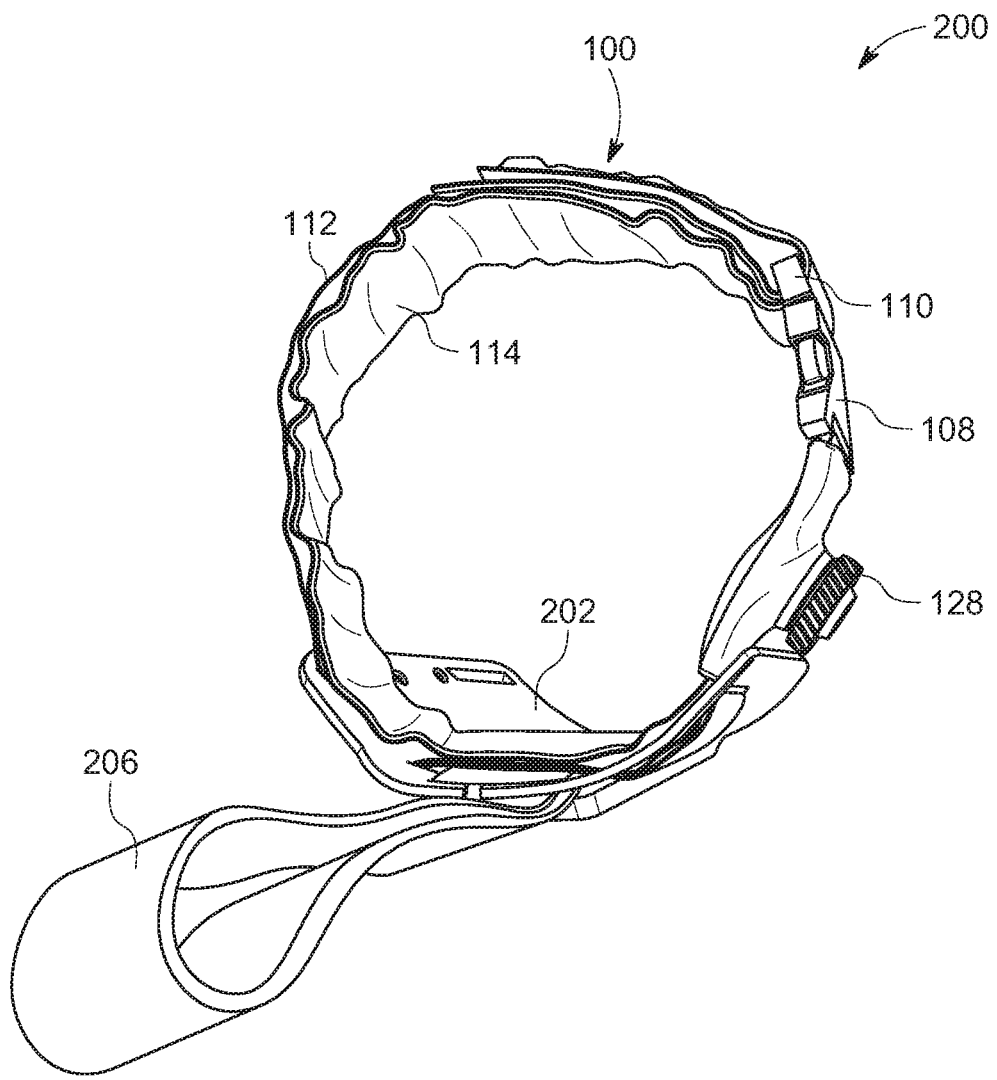
FIG. 6A is a top perspective view of the holster-tourniquet equipment of FIGS. 5A-5B showing the bands connected to form a loop (such as around a user's leg), where the internal band has not been tensioned and is connected to the outer band.
Figure 6B:
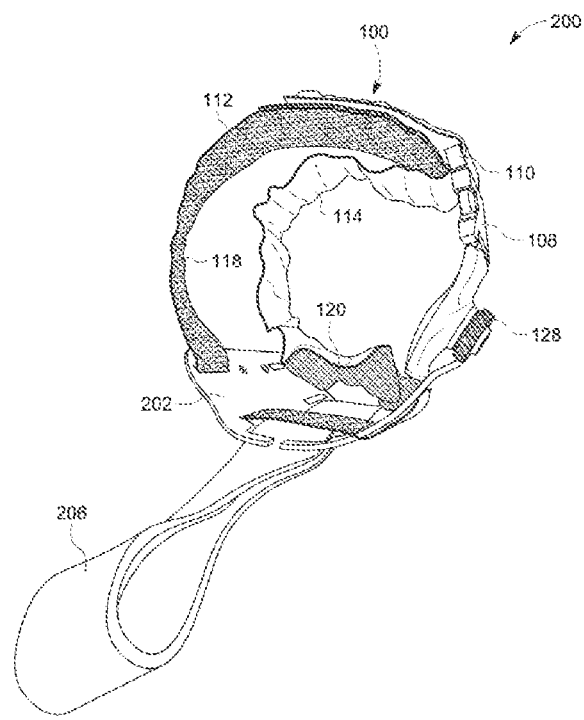
FIG. 6B is a top perspective view of the holster-tourniquet equipment of FIG. 6A with the internal band of the tourniquet assembly of FIG. 1 partially separated from the external band therein with the circumference formed by the internal band being reduced due to the internal band being tensioned.

FIGS. 6A and 6B depict the holster-tourniquet equipment 200 in its normal state (i.e., not tensioned) and actuated state (i.e., tensioned to apply the tourniquet), respectively. In the normal state, as depicted in FIG. 6A, the tourniquet assembly 100 forms a loop with the first connecting member 108 attached to the second connecting member 110. The holster-tourniquet equipment 200 is generally worn by the user in its normal state. When the user has been injured and needs to apply the tourniquet, the holster-tourniquet equipment 200, the user actuates the tensioning member 106 (such as the a rotatable version in FIGS. 1-9, or windlass version in FIGS. 10-12) to its actuated state. For this purpose, the user provides tension to the internal band 114 to update by reducing the slack therein, by rotating or turning the tensioning member 106 therein. In the actuated state, as depicted in FIG. 6B, the internal band 114 of the tourniquet assembly 100 is partially separated from the external band 112 therein with the circumference formed by the internal band 114 being reduced. This reduced circumference of the internal band 114 applies the pressure on the injured limb which is transferred to the walls of vessels in the limb, causing them to compress, constrict, and become temporarily occluded.

Herein, the circumference formed by the internal band 114 is reduced when the tensioning member 106 is actuated, thereby compressing the limb when the tourniquet assembly 100 is placed around the limb, and thereby reducing blood flow to the limb. Further, herein, the internal band 114 at least partially separates from the external band 112 when the tensioning member 106 is actuated due to direct tension being applied to the internal band 114 from the tensioning member 106, but no direct tension being applied to the external band 112. In an example, the internal band 114 with the reduced circumference can have a diameter that can apply sufficient pressure to constrict or occlude blood flow from the limb, while preventing the internal band 114 from constricting the limb to the point of injury and/or amputation. In some examples, the internal band 114 with the reduced circumference can have a diameter of three to seven inches. In other examples, the internal band 114 with the reduced circumference can have a smaller diameter, a larger diameter, or vary in diameter.

Figure 7A:
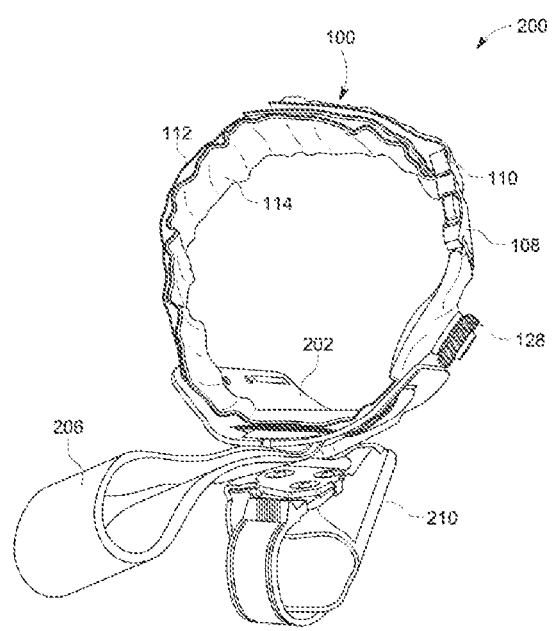
FIG. 7A is top perspective view of the holster-tourniquet equipment of FIGS. 5A-5B with a gun holster attached therewith and the internal band is connected to the outer band.
Figure 7B:
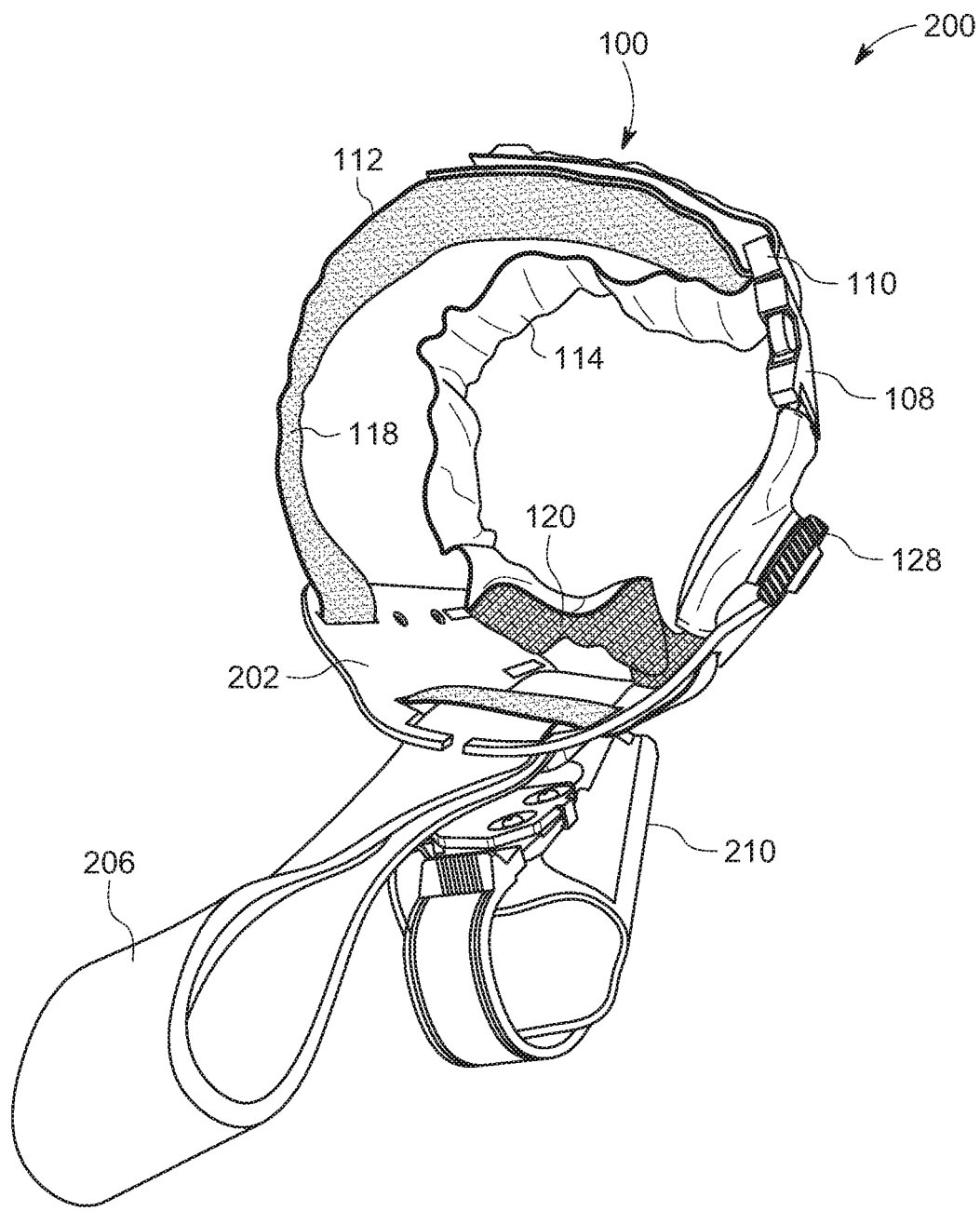
FIG. 7B is a top perspective view of the holster-tourniquet equipment of FIGS. 5A-5B with the internal band of the tourniquet assembly of FIG. 1 partially separated from the external band therein with the circumference formed by the internal band being reduced due to the internal band being tensioned.

FIGS. 7A and 7B depict the holster-tourniquet equipment 200 in its normal state and actuated state, respectively, with a gun holster 210 removably connected therewith. The gun holster 210 is generally connected to the plate 202 of the holster-tourniquet equipment 200. As discussed, the holster-tourniquet equipment 200 forms part of gear equipment worn by a user, such as a police or military personnel. The holster-tourniquet equipment 200 while allowing the equipment, such as the gun holster 210 to be carried, can also be used and applied as a tourniquet as discussed in reference to FIGS. 6A-6B by disposing the holster-tourniquet equipment 200 from its normal state to actuated state.

FIG. 8 depicts the holster-tourniquet equipment 200 being used as a gun holster arranged on a thigh of a leg of a user. Herein, the plate 202 of the holster-tourniquet equipment 200 is adapted to be arranged on a thigh of the leg of the user such that the internal band 114 of the tourniquet assembly 100 forms a loop around the thigh of the leg of the user.

Herein, the plate 202 includes means for receiving the gun holster 210 thereon. FIG. 9 depicts the holster-tourniquet equipment 200 being used as a shoulder pad arranged on an upper arm of a user. Herein, the plate 202 of the holster-tourniquet equipment 200 is in the form of a shoulder pad 212 adapted to be arranged on an upper arm of a user such that the internal band 114 of the tourniquet assembly 100 forms a loop around the upper arm of the user. For this purpose, as depicted, the one or more channels 204 are in the form of loops formed on the shoulder pad 212. In other embodiments, the holster-tourniquet equipment can be used without a holster, or any gear, and the strap 102 can be worn around the arm using Velcro, or other attachment means, sewn into combat shirts.

FIGS. 10-12 depicts a tourniquet assembly and a corresponding holster-tourniquet equipment, in accordance with another embodiment of the present disclosure. FIG. 10 depicts a tourniquet assembly 1000 with a tensioning member 1002. The tourniquet assembly 1000 is similar to the tourniquet assembly 100 (as explained in the preceding paragraphs) except the tensioning member 1002 being used therein includes a windlass (instead of the dial 128) for providing tension in order to use the tourniquet assembly 1000 as an emergency tourniquet. FIG. 11 depicts a holster-tourniquet equipment 1100 with the tourniquet assembly 1000. The holster-tourniquet equipment 1100 is again similar to the holster-tourniquet equipment 200 (as explained in the preceding paragraphs) except the tourniquet assembly 1000 with the tensioning member 1002 being used therein includes the windlass (instead of the dial 128) for providing tension in order to use the tourniquet assembly 1000 as an emergency tourniquet. FIG. 12 depicts the holster-tourniquet equipment 1100 being used as a gun holster arranged on a thigh of a leg of a user.

The present tourniquet assembly 100, 1000 can be used as a load bearing strap for the holster-tourniquet equipment 200, 1100 as well as an emergency tourniquet, which is especially advantageous in military settings. When a victim is injured, blood loss can be a significant case of death. Therefore, the ability to stop the blood loss from an injury is critical to survival for various injuries. Preventable death occurs when the injured party does not receive medical treatment and more specifically, when the blood loss is not stopped in a timely fashion. Tourniquets are devices that can control venous and arterial circulation to extremities. In operation, tourniquets apply pressure circumferentially upon skin and underlying tissues of a limb. The pressure transfers to the walls of vessels, causing them to compress, constrict, and become temporarily occluded. To avoid further injury to the limb, the tourniquet pressure should be sufficient to stop blood flow, but should not be strong enough to damage tissue, nerves, and/or blood vessels. The present tourniquet assembly 100, 1000 being part of the gear worn by a user can be used in a timely fashion. Further, the tourniquet assembly 100, 1000 can be operated one-handed to apply the tourniquet in the event that the injury is sustained on one arm. Further, if the emergency occurs and the injured person is alone, the individual must be able to apply the tourniquet to himself and in some cases one-handed using the tourniquet assembly 100, 1000 of the present disclosure.

One main advantage of using a strap that has an internal band and external band, where the internal band is used to reduce blood supply is that if a single band were used that both held the equipment (such holding the plate 202) of the holster 210, is that if this single band were tightened, the entire plate, having a large surface area would be compressed against the user's leg. Compressing an object with a large surface area against arteries or veins would not provide enough constriction to reduce blood flow. It is the combination of an external strap that holds the plate 202 against the leg with an internal strap having a small width, that allows the user to wear attached gear comfortably, but provide means to apply a tourniquet to reduce blood flow, while not changing the pressure of the plate 202 against the user's leg.

Another advantage is that the user can apply the tourniquet without having to remove attached gear, since the tourniquet assembly 100 and holster-tourniquet equipment 200 are integrated into one unit.

REFERENCE NUMBERS

The following reference numbers are used throughout FIGS. 1-12:
- 100 tourniquet assembly
- 102 strap portion
- 104 locking arrangement
- 106 tensioning member
- 109 D-ring
- 108 first connecting member
- 110 second connecting member
- 112 external band
- 112a proximal end of external band
- 112b distal end of external band
- 112c inner surface of external band
- 112d outer surface of external band
- 114 internal band
- 114a proximal end of internal band
- 114b distal end of internal band
- 114c outer surface of internal band
- 114d inner surface of internal band
- 116 affixed portion
- 118 first semi-permanent adhesive member
- 120 second semi-permanent adhesive member
- 122 length of the external band
- 124 slots
- 126 grommet
- 127 hole
- 128 dial
- 200 holster-tourniquet equipment 200
- 202 plate
- 204 channels
- 206 belt loop
- 208 second strap
- 210 gun holster
- 212 shoulder pad
- 1000 tourniquet assembly (second embodiment)
- 1002 tensioning member (windlass) (second embodiment)
- 1100 holster-tourniquet equipment (second embodiment)

While the invention has been described in terms of exemplary embodiments, it is to be understood that the words that have been used are words of description and not of limitation. As is understood by persons of ordinary skill in the art, a variety of modifications can be made without departing from the scope of the invention defined by the following claims, which should be given their fullest, fair scope.

What is claimed is:

1. A tourniquet assembly comprising:
   (a) an external band having a proximal end, a distal end, an inner surface, and an outer surface,
      wherein the inner surface of the external band includes a first semi-permanent adhesive member, wherein the external band forms an external loop having an external loop circumference;

wherein the external band has a first connecting member affixed to the proximal end of the external band;

(b) an internal band having a proximal end fixedly attached to the proximal end of the external band, a distal end removably engaged to the distal end of the external band, an inner surface, and an outer surface, the internal band is adapted for constricting blood flow in a limb, wherein the inner surface of the internal band includes a second semi-permanent adhesive member removably engaged to the first semi-permanent adhesive member along a length of the external band, whereby the first and second semi-permanent adhesive members can easily be pulled apart and adhered together numerous times without substantial loss of adhesive properties, wherein the internal band is designed to form an internal loop having an internal circumference around a limb when the internal band is placed around the limb;

and, (c) a tensioning member connected to the internal band and configured to apply direct tension to the internal band without applying direct tension to the external band;

wherein the internal loop circumference is reduced relative to the external loop circumference when the tensioning member is actuated, thereby compressing the limb when the tourniquet assembly is placed around the limb, and thereby reducing blood flow to the limb; and, wherein the internal band at least partially separates from the external band when the tensioning member is actuated due to direct tension being applied to the internal band from the tensioning member, but no direct tension being applied to the external band;

wherein the internal band at least partially separates from the external band when the tensioning member is actuated due to direct tension being applied to the internal band from the tensioning member.

2. The tourniquet assembly of claim 1, wherein the external band and the internal band are sewn together along a portion of lengths thereof at the respective proximal ends.

3. The tourniquet assembly of claim 1, wherein the first connecting member is affixed to the proximal ends of the external band and the internal band.

4. The tourniquet assembly of claim 1, further comprising a second connecting member removably connected to the distal end of the external band, wherein the external band forms a loop when the first connecting member is attached to the second connecting member, and wherein the external band and the internal band are adapted to be adhered together at least at the respective distal ends, with the second connecting member connected thereto, to allow for the tourniquet assembly to form a loop when the first connecting member is attached to the second connecting member.

5. The tourniquet assembly of claim 4, wherein the external band and the internal band are adapted to be pulled apart at least at respective distal ends, with the second connecting member disconnected therefrom, to allow for the tourniquet assembly, at the distal end of the external band and the internal band, to guide through one or more channels in a plate of a holster-tourniquet equipment.

6. The tourniquet assembly of claim 5, wherein the external band and the internal band are adapted to be adhered back together at least at respective distal ends, with the second connecting member connected thereto, after guiding of the tourniquet assembly through one or more channels in the plate of the holster-tourniquet equipment, to affix the tourniquet assembly in the holster-tourniquet equipment.

7. The tourniquet assembly of claim 6, wherein the second connecting member includes at least two slots formed therein, and wherein the external band and the internal band at distal ends thereof, when adhered back together, are adapted to pass through the at least two slots in the second connecting member to adjust a circumference of the loop formed by the external band when the first connecting member is attached to the second connecting member.

8. The tourniquet assembly of claim 1, wherein the tensioning member includes a dial configured to be rotated to cause the internal band to uptake for applying direct tension to the internal band without applying direct tension to the external band.

9. The tourniquet assembly of claim 1, wherein the tensioning member includes a windlass configured to be turned to cause the internal band to uptake for applying direct tension to the internal band without applying direct tension to the external band.

10. The tourniquet assembly of claim 1, wherein the tensioning member is placed over the outer surface of the external band for quick access by a user, and wherein the external band includes a grommet inserted into a hole therein to allow for the tensioning member to be connected to the internal band and apply direct tension thereto without applying direct tension to the external band.

11. The tourniquet assembly of claim 1, wherein the first and second semi-permanent adhesive members are hook-and-loop based fasteners.

12. The tourniquet assembly of claim 4, wherein the first connecting member is one of a male buckle part and a female buckle part, and the second connecting member is other of the male buckle part and the female buckle part, to allow for the first connecting member and the second connecting member to attach with each other.

13. An apparatus comprising:

(a) a plate having at least two channels formed therein; and, (b) a tourniquet assembly comprising:

(i) an external band engaged to the plate, the external band extends through the at least two channels and support the plate and having a proximal end, a distal end, an inner surface, and an outer surface adapted to abut the plate, wherein the inner surface of the external band includes a first semi-permanent adhesive member, wherein the external band has a first connecting member affixed to the proximal end of the external band;

wherein the external band forms an external loop having an external loop circumference;

(ii) an internal band having a proximal end fixedly attached to the proximal end of the external band, a distal end removably engaged to the distal end of the external band, an inner surface, and an outer surface, the internal band is arranged away from the plate such that a portion of the external band extending between the at least two channels is disposed between the plate and the internal band, wherein the internal band is adapted for constricting blood flow in a limb, wherein the inner surface of the internal band includes a second semi-permanent adhesive member removably engaged to the first semi-permanent adhesive member along a length of the external band, whereby the first and second semi-permanent adhesive members can easily be pulled apart and adhered together numerous times without substantial loss of adhesive properties, wherein the internal band is designed to form an internal loop having an internal loop circumference around a limb when the internal band is placed around the limb, wherein the external band and the internal band are adapted to be pulled apart at least from the respective distal ends, to allow for the tourniquet assembly, at the distal end of the external band, to guide through the at least two channels in the plate of the apparatus; and, (iii) a tensioning member connected to the internal band and configured to apply direct tension to the internal band without applying direct tension to the external band;

wherein the internal loop circumference is reduced relative to the external loop circumference when the tensioning member is actuated, thereby compressing the limb when the tourniquet assembly is placed around the limb, and thereby reducing blood flow to the limb; and, wherein the internal band at least partially separates from the external band when the tensioning member is actuated due to direct tension being applied to the internal band from the tensioning member, but no direct tension being applied to the external band;

wherein the internal band at least partially separates from the external band when the tensioning member is actuated due to direct tension being applied to the internal band from the tensioning member.

14. The apparatus of claim 13, further comprising a gun holster configured to receive a gun, wherein the plate is adapted to be arranged on a thigh of a leg of a user such that the internal band of the tourniquet assembly forms a loop around the thigh of the leg of the user, and wherein the plate is connected to the gun holster, thereby forming a holster-tourniquet equipment.

15. The apparatus of claim 13, wherein the plate is in a form of a shoulder pad adapted to be arranged on an upper arm of a user such that the internal band of the tourniquet assembly forms a loop around the upper arm of the user, and wherein the one or more channels are in the form of loops formed on the shoulder pad.

16. The apparatus of claim 13, further comprising a second connecting member removably connected to the distal end of the external band, wherein the external band forms a loop when the first connecting member is attached to the second connecting member, and wherein the external band and the internal band are adapted to be adhered together at least at the respective distal ends, with the second connecting member connected thereto, to allow for the tourniquet assembly to form a loop when the first connecting member is attached to the second connecting member.

17. The apparatus of claim 16, wherein the external band and the internal band are adapted to be adhered back together at least at respective distal ends, with the second connecting member connected thereto, after guiding of the tourniquet assembly through the at least two channels in the plate to affix the tourniquet assembly.

18. The apparatus of claim 17, wherein the second connecting member includes at least two slots formed therein, and wherein the external band and the internal band at the distal ends thereof, when adhered back together, are adapted to pass through the at least two slots in the second connecting member to adjust a circumference of the loop formed by the external band when the first connecting member is attached to the second connecting member.

19. The apparatus of claim 13, wherein the tensioning member includes a dial configured to be rotated to cause the internal band to uptake for applying direct tension to the internal band without applying direct tension to the external band.

20. The apparatus of claim 13, wherein the tensioning member includes a windlass configured to be turned to cause the internal band to uptake for applying direct tension to the internal band without applying direct tension to the external band.

* * * * *